(12) United States Patent
Zheng

(10) Patent No.: US 9,969,682 B2
(45) Date of Patent: May 15, 2018

(54) FUNCTIONALIZED GRAPHENE BARRIER ELEMENT

(71) Applicant: Nitto Denko Corporation, Osaka (JP)

(72) Inventor: Shijun Zheng, San Diego, CA (US)

(73) Assignee: NITTO DENKO CORPORATION, Osaka (JP)

(*) Notice: Subject to any disclaimer, the term of this patent is extended or adjusted under 35 U.S.C. 154(b) by 0 days. days.

(21) Appl. No.: 15/073,323

(22) Filed: Mar. 17, 2016

(65) Prior Publication Data

US 2016/0272575 A1  Sep. 22, 2016

Related U.S. Application Data

(60) Provisional application No. 62/134,501, filed on Mar. 17, 2015.

(51) Int. Cl.

| | | |
|---|---|---|
| *C07C 233/34* | (2006.01) | |
| *C01B 31/04* | (2006.01) | |
| *C08K 3/04* | (2006.01) | |
| *C08K 9/04* | (2006.01) | |
| *B65D 65/38* | (2006.01) | |
| *C07D 303/46* | (2006.01) | |
| *B32B 9/00* | (2006.01) | |
| *B32B 27/22* | (2006.01) | |
| *B32B 27/28* | (2006.01) | |
| *B32B 27/30* | (2006.01) | |
| *C01B 32/23* | (2017.01) | |
| *C01B 32/194* | (2017.01) | |

(52) U.S. Cl.
CPC ............ *C07C 233/34* (2013.01); *B32B 9/007* (2013.01); *B32B 27/22* (2013.01); *B32B 27/281* (2013.01); *B32B 27/30* (2013.01); *B32B 27/304* (2013.01); *B32B 27/306* (2013.01); *B32B 27/308* (2013.01); *B65D 65/38* (2013.01); *C01B 32/194* (2017.08); *C01B 32/23* (2017.08); *C07D 303/46* (2013.01); *C08K 3/042* (2017.05); *C08K 9/04* (2013.01); *B32B 2255/26* (2013.01); *B32B 2270/00* (2013.01); *B32B 2274/00* (2013.01); *B32B 2307/412* (2013.01); *B32B 2307/7242* (2013.01); *B32B 2307/732* (2013.01); *C08K 2201/008* (2013.01); *C08K 2201/011* (2013.01)

(58) Field of Classification Search
CPC ........ B32B 27/00; B32B 27/18; B65C 65/38; C01B 31/043; C01B 31/0484; C07C 233/34; C07C 2103/54; C07D 303/46; C08K 3/04; C08K 9/04; C08K 2201/008; C08K 2201/011

See application file for complete search history.

(56) References Cited

U.S. PATENT DOCUMENTS

| | | |
|---|---|---|
| 7,745,528 B2 | 6/2010 | Prud'Homme et al. |
| 7,923,491 B2 | 4/2011 | Weng et al. |
| 8,110,026 B2 | 2/2012 | Prud'Homme et al. |
| 8,663,762 B2 | 3/2014 | Mazany et al. |
| 2006/0030483 A1 | 2/2006 | Jang |
| 2007/0131915 A1 | 6/2007 | Stankovich et al. |
| 2010/0096597 A1 | 4/2010 | Prud'Homme et al. |
| 2011/0223405 A1 | 9/2011 | Compton et al. |
| 2012/0171093 A1 | 7/2012 | Swager et al. |
| 2012/0282419 A1 | 11/2012 | Ahn et al. |
| 2012/0315407 A1 | 12/2012 | Mazany et al. |
| 2013/0059155 A1 | 3/2013 | Choi et al. |
| 2013/0295367 A1 | 11/2013 | Compton et al. |
| 2013/0305927 A1 | 11/2013 | Choi et al. |
| 2014/0069277 A1 | 3/2014 | Choi et al. |
| 2014/0272350 A1* | 9/2014 | Kim ...................... C23C 16/26 428/213 |
| 2014/0370246 A1 | 12/2014 | Hurt |
| 2015/0004667 A1* | 1/2015 | McKinney ............ C07K 17/14 435/188 |

FOREIGN PATENT DOCUMENTS

| | | |
|---|---|---|
| CN | 102115566 A | 7/2011 |
| EP | 1892089 | 2/2008 |
| KR | 10-1209293 B1 | 12/2012 |
| KR | 2013-0025168 A | 3/2013 |
| KR | 10-1308967 B1 | 9/2013 |
| KR | 2013-0128686 A | 11/2013 |
| WO | 2008/130431 A2 | 10/2008 |
| WO | 2011/087301 A2 | 7/2011 |
| WO | 2013/062246 A1 | 2/2013 |
| WO | 2013/107229 A1 | 7/2013 |
| WO | 2014142757 | 9/2014 |

OTHER PUBLICATIONS

Tang, et al. "Enhanced Thermal Stability in Graphene oxide covalently functionalized with 2-amino-4,6-didodecylamino-1,3,5-triazine" Carbon, vol. 49, No. 4, Apr. 1, 2011, pp. 1258-1265.
International Search Report and Written Opinion dated Jul. 4, 2016 for PCT/US2016/022935.
Chen, J., et al., "Enhancing polymer/graphene oxide gas barrier film properties by introducing new crystals", Carbon, vol. 75, 2014, pp. 443-451.
Jang, J. et al., "Dispersibility of reduced alkylamine-functionalized graphene oxides in organic solvents", Journal of Colloid and Interface Science, vol. 424, 2014, pp. 62-66.

(Continued)

*Primary Examiner* — Pancham Bakshi
*Assistant Examiner* — Mark R Luderer
(74) *Attorney, Agent, or Firm* — Maschoff Brennan; Brent A. Johnson; Yuefen Zhou

(57) ABSTRACT

Described herein are functionalized graphene compositions that have gas, fluid, and/or vapor resistant properties. Also described are barrier elements based on the aforementioned compositions. Also described is a barrier device that incorporates the barrier element and further comprises a substrate and a protective coating, encompassing the barrier element.

20 Claims, 1 Drawing Sheet

(56) References Cited

OTHER PUBLICATIONS

Jang, J., et al., "Effects of the alkylamine functionalization of graphene oxide on the properties of polystyrene nanocomposites", Nanoscale Research Letters, vol. 9, No. 265, 2014, pp. 1-6.
Nair, R.R., et al., "Unimpeded permeation of water through helium-leak-tight graphene-based membranes", Science, vol. 335, No. 6067, 2012, pp. 442-444.
Bunch, S. J., et al., "Impermeable Atomic Membranes from Graphene Sheets", Nano Letters, vol. 8, No. 8, 2008, pp. 2458-2462.
Yang, X., et al., "Synthesis and characterization of alkylamine-functionalized graphene for polyolefin-based nanocomposites", Applied Surface Science, vol. 305, 2014, pp. 725-731.

* cited by examiner

FUNCTIONALIZED GRAPHENE BARRIER ELEMENT

BACKGROUND

Field

The present disclosure relates to functionalized graphene compositions and their application as gas-barrier and/or moisture-barrier elements.

Description of Related Art

In the area of packaging, barrier films provide a lower-cost method as compared to cans and other packaging. In wide use is nontransparent metal-based films that consist of metalized polymers or a based on aluminum foil. However, such films typically do not enable customers to view the product to verify quality before purchase. In addition, metal-based packaging may not be microwaveable, limiting the manufacturer's ability to sterilize the product by microwave sterilization. Additional considerations for plastic packaging are a desire to avoid the presence of chlorine for purposes of recycling and a desire to avoid using Bisphenol A (BPA) due to market demand and perceived health risk. As a result, current transparent barrier-films consist of Polyvinylidine Chloride (PVDC), PVC, Ethylene Vinyl Alcohol (EVOH), Polyvinyl Alcohol (PVA), low density polyethylene (LDPE), or films with ceramic coatings like Silicone Oxides (SiOx) or Aluminum Oxides (AlOx).

As products require longer shelf-lives, the need for in-packaging sterilization and for packaging to be efficient barriers of oxygen and water have become driving considerations. To help address oxygen permeation into the PET barrier films three main barrier technologies have been developed: co-injection, coatings, and oxygen scavengers. The resulting barriers tend to be complex with many layers.

Consequently, there is a need for a low-cost coating with strong barrier properties, high mechanical strength but that is flexible, metal-free and microwaveable.

SUMMARY

One solution is utilizing a nanocomposite barrier film based on graphene-oxide. Some graphene membranes may be impermeable to most gases, including helium. However, sub-micrometer thick graphene membranes—while practically impermeable to most liquids, vapors, and gases, including helium—allow unimpeded permeation of water.

The embodiments disclosed herein include a high-strength material that can be used in packaging where a transparent vapor barrier and gas barrier is desired for storage consumables. The present embodiments also include a barrier element that is useful in applications where gas, vapor, and/or fluid permeability can be minimized, such as in food packaging applications.

Some embodiments include a graphene compound comprising an optionally functionalized graphene directly bonded to —NH—R—NHCOR' or —CO—NH—R—NH-COR'; wherein R is optionally substituted $C_{1-20}$ hydrocarbylene; and R' is optionally substituted $C_{1-30}$ hydrocarbyl or $C_{3-30}$ heteroaryl.

Some embodiments include a barrier element comprising a functionalized graphene compound as described herein, wherein the barrier element is transparent.

Also disclosed herein is clear packaging comprising a functionalized graphene compound or a barrier element as described herein.

Some embodiments include a product wrapped in the clear packaging as described herein.

These and other embodiments are described in greater detail below.

DETAILED DESCRIPTION

Figure 1:
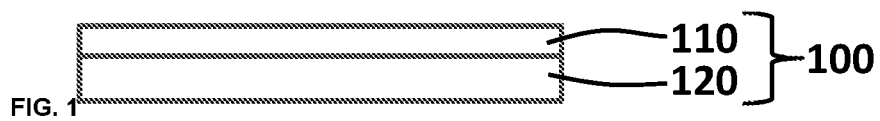
FIG. 1 is a schematic of an embodiment of a barrier device described herein.

The optionally functionalized graphene may be any type of graphene, including unfunctionalized graphene and functionalized graphene, or graphene that that has been oxidized, reduced, or otherwise reacted (e.g. by adding across a C=C bond, replacing a group formed by oxidation, etc.). Examples of oxidized graphene include graphene oxide, reduced graphene oxide, etc.

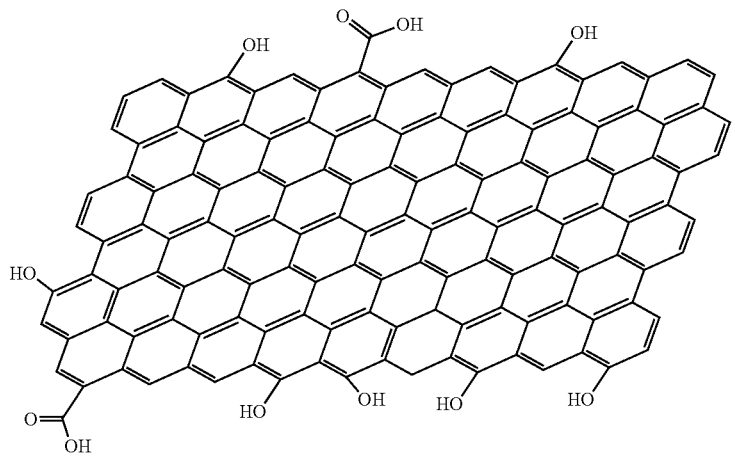 [SMILES: O=C(O)c1cc2cc(O)c3c4ccc5c6cccc7c(O)c8cc9c(C(=O)O)c%10cc%11cc%12c(O)c%13cc%14ccc%15ccc%16c%17ccc%18c%19ccc(O)c%20cc%21c(O)c%22c%23c%24c%21c(c%20%19)c%19c%18c%17c%17c%18c%16c%15c%14c%14c%13c%13c%12c%12c%11c%11c%10c%10c9c9c8c(c76)c6c5c4c4c5c3c2c2c1cc1cc3c(O)c7c(O)c(c8c%15c7c7c3c3c1c2c5c1c3c2c7c3c%15c5c(c7c%24c%19c%17c%15c7c7c5c5c3c3c(c%11c5c%12c7c%13c%15c%14%18)c%10c5c9c6c4c1c5c23)C%238)C%22]

Non-Limiting Example of a Structure of a Reduced Graphene Oxide [RGO]

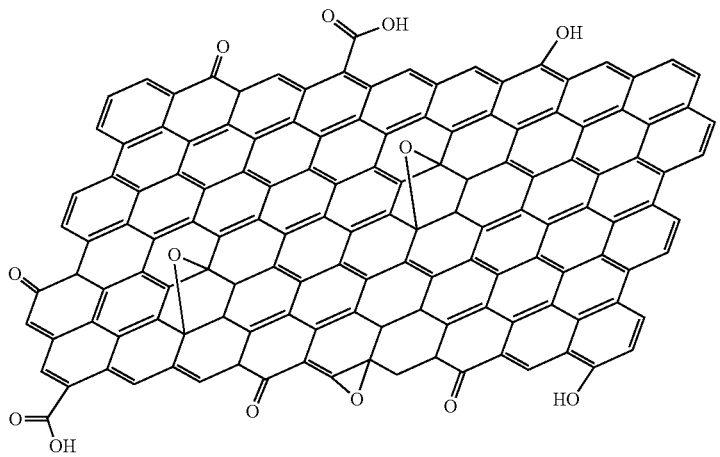 [SMILES: O=C(O)c1cc2c3c4c5c6c7c3c1=CC1=CC3C(=O)C8=C9OC9%10CC9C(=O)c%11cc%12c(O)ccc%13c%14ccc%15c%16ccc%17ccc%18cc%19c(O)c%20cc%21cc%22c(C(=O)O)c%23c%24c%25c%26c%27c%28c(cccc%28c%28ccc(c%29c-5c5c%30c%31c%32c%33c%34c(c8c8c%35c%34c%34c%36c%37c%38c(c%21c%21c%20c%20c%39c%40c%41c%42c%43c%44c(c%11c(c%12%13)c%11c%44c%41c(c%15c%14%11)c%11c%16c%17c%18c(c%19%20)c%40%11)=C9C(C%43=C%35[C@]%369O[C@]%21%37C%39C%429)C8%10)c%22c%24c(c%38c%34%32)c%31c%25c5c%27c%29%28)=C3C3C%33[C@]6%30O[C@@]173)C4C(=O)C=2)C(=O)C%26C=%23]

Non-Limiting Example of a Structure of a Graphene Oxide [GO]

Oxidized graphene oxides may be functionalized, for example, by replacing an OH, =O, epoxy, or $CO_2H$ with a different functional group such as F, Cl, Br, =NH, $NH_2$, etc.

In some embodiments, a functionalized graphene may have, or may only have, functional or substituent groups which are H, or which have a molecular weight of about 12 g/mol to about 100 g/mol, to about 200 g/mol, or to about 300 g/mol, such as $C_{1-12}$ hydrocarbyl or $C_{1-6}$ hydrocarbyl (e.g. $CH_3$, ethyl, ethenyl, ethynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.), $C_{1-12}H_{0-27}O_{1-3}N_{1-3}F_{1-3}Cl_{0-1}Br_{0-1}$ heteroalkyl, OH, $NH_2$, or halo. In some embodiments, a functionalized graphene may have, or may only have, functional or substituent groups which are H, —OH, —O—, epoxy, =O, —$CO_2H$, COH, $C_{1-6}$—$CO_2$-alkyl (e.g. —$CO_2CH_3$, —$CO_2C_2H_5$, —$CO_2C_3H_7$, etc.), —O-alkyl (e.g. —O—$CH_3$, —O—$C_2H_5$, —O—$C_3H_7$, etc.), F, Cl, Br, $CF_3$, $C_{1-6}$ alkyl, CN, $NH_2$, —NH—R—NHCOR', or —CO—NH—R—NHCOR'.

The optionally functionalized graphene is directly bonded to:

—NH—R—NHCOR' (Formula 1) or,

—CO—NH—R—NHCOR' (Formula 2).

With respect to any relevant structural representation, such as Formula 1 or Formula 2, R is optionally substituted $C_{1-20}$ hydrocarbylene, such as alkylene (e.g. —$CH_2$—; $C_2$ alkylene, such as —$CH_2CH_2$—, —$CH(CH_3)$—, etc.; $C_3$ alkylene; $C_4$ alkylene; $C_5$ alkylene; $C_6$ alkylene; $C_7$ alkylene; $C_8$ alkylene; $C_9$ alkylene; $C_{10}$ alkylene; $C_{11}$ alkylene; $C_{12}$ alkylene; $C_{13}$ alkylene; $C_{14}$ alkylene; $C_{15}$ alkylene; $C_{16}$ alkylene; $C_{17}$ alkylene; $C_{18}$ alkylene; $C_{19}$ alkylene; $C_{20}$ alkylene), alkenylene (e.g. —$(CH_2)_n$CH=CH—$(CH_2)_o$—, wherein n+o is 0, 1, 2, 3, 4, 5, 6, 7, 8, 9, 10, 11, 12, 13, 14, 15, 16, 17, or 18), arylene, such as phenylene, etc. In some embodiments, R is $C_{1-12}$ alkylene. In some embodiments, R is —$(CH_2)_8$—

With respect to any relevant structural representation, such as Formula 1 or Formula 2, R' is optionally substituted $C_{1-30}$ hydrocarbyl such as alkyl, e.g. linear, branched, or cycloalkyl, or a combination thereof, having 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms (including methyl, ethyl, propyl isomers, butyl isomers, cyclobutyl isomers, pentyl isomers, cyclopentyl isomers, hexyl isomers, cyclohexyl isomers, heptyl isomers, cycloheptyl isomers, octyl isomers, cyclooctyl isomers, nonyl isomers, cyclononyl isomers, decyl isomers, cyclodecyl isomers. undecyl isomers, cycloundecyl isomers, dodecyl isomers, cyclododecyl isomers, tridecyl isomers, cyclotridecyl isomers, tetradecyl isomers, cyclotetradecyl isomers, pentadecyl isomers, cyclopentadecyl isomers, hexadecyl isomers, cyclohexadecyl isomers, heptadecyl isomers, cycloheptadecyl isomers, octadecyl isomers, cyclooctadecyl isomers, nonadecyl isomers, cyclononadecyl isomers, eicosyl isomers, cycloeicosyl isomers, etc.). In some embodiments, R' is —$(CH_2)_qCH_3$, where q is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

As used herein the term "aryl" has the broadest meaning generally understood in the art, and may include an aromatic ring or aromatic ring system. Exemplary non-limiting aryl groups are phenyl, naphthyl, acenaphthyl, etc. "$C_{6-30}$ aryl" refers to aryl where the ring or ring system has from 6-30 carbon atoms. "$C_{6-30}$ aryl" does not characterize or limit any substituents attached to the ring atoms. As used herein, the term "heteroaryl" also has the meaning understood by a person of ordinary skill in the art, and in some embodiments, may refer to an "aryl" which has one or more heteroatoms in the ring or ring system. Non-limiting "heteroaryl" groups may include, but are not limited to, pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc. "$C_{6-30}$ heteroaryl" refers to aryl where the ring or ring system has from 6-30 carbon atoms. "$C_{6-30}$ heteroaryl" does not characterize or limit any substituents attached to the ring atoms.

A graphene platelet may have any suitable number of groups of —NH—R—NHCOR' or —CO—NH—R—NHCOR' attached. For example, some functionalized graphene compounds may have a total number of —NH—R—NHCOR' or —CO—NH—R—NHCOR' groups (i.e. the number of —NH—R—NHCOR' groups plus the number of —CO—NH—R—NHCOR' groups) that is about 1-10, about 1-3, about 3-6, about 6-10, about 1-5, about 2-5, or about 2-4 total groups of per 100 graphene carbon atoms.

For example, some functionalized graphene compounds may have a molar ratio of nitrogen to carbon that is about 0.001-0.2 (0.001-0.2 moles of nitrogen for each mole of carbon), about 0.001-0.02, about 0.02-0.04, about 0.04-0.06, about 0.06-0.08, about 0.08-0.1 about 0.1-0.12, about 0.12-0.14, about 0.14-0.16, about 0.16-0.18, about 0.18-0.2, about 0.02-0.08, about 0.03-0.06, 0.033, 0.056, or any molar ratio in a range bounded by any of these values.

Some functionalized graphene compounds may have a molar ratio of oxygen to carbon that is about 0.01-1 (0.01-1 moles of oxygen for each mole of carbon), about 0.01-0.2, about 0.2-0.4, about 0.4-0.6, about 0.6-0.8, about 0.8-0.1 about 0.1-0.12, about 0.12-0.14, about 0.14-0.16, about 0.16-0.18, about 0.2-0.6, about 0.2-0.8, about 0.3-0.6, 0.25, 0.57, or any molar ratio in a range bounded by any of these values.

Some functionalized graphene compounds may be represented by an empirical formula $C_{100-200}H_{60-120}N_{1-10}O_{20-100}$, $C_{110-150}H_{70-110}N_{3-9}O_{30-70}$, $C_{120-130}H_{80-85}N_4O_{65-75}$, $C_{140-150}H_{100-105}N_8O_{30-40}$, $C_{123}H_{82}N_4O_{70}$, or $C_{142}H_{102}N_8O_{35}$.

A functionalized graphene compound attached to a group represented by Formula 1 or Formula 2 (referred to herein as a "subject compound") may be used in a barrier element, such as a transparent barrier element. Such a barrier element can provide desired gas, fluids, and/or vapor permeability resistance. The barrier element can comprise a single layer containing the subject compound, or can include multiple layers. The subject compound can provide beneficial barrier characteristics for multiple reasons including: increasing the solubility in solvents for ease of fabrication, manipulating the hydrophobic properties of the graphene to increase water vapor barrier qualities, and increasing the inter-graphene interactions to manipulate the water vapor barrier properties and/or structural properties of the resultant barrier.

In some embodiments, a gas permeability of the barrier element, such as oxygen permeability, can be less than 0.100 cc/m$^2$·day, less than 0.010 cc/m$^2$·day, or less than 0.005 cc/m$^2$·day. See United States Patent Publication US 2014/0272350, ASTM D3985, ASTM F1307, ASTM 1249, ASTM F2622, and/or ASTM F1927, for their disclosure related to determining gas (oxygen) permeability %, e.g., oxygen transfer rate (OTR).

In some embodiments, the moisture permeability of the barrier element can be less than 10.0 gm/m$^2$·day, 5.0 gm/m$^2$·day, 3.0 gm/m$^2$·day, and/or 2.5 gm/m$^2$·day. In some embodiments, the moisture permeability can be measured by water vapor permeability/transfer rate at the above described levels. See Caria, P. F., Ca test of Al$_2$O$_3$ gas diffusion barriers grown by atomic deposition on polymers, APPLIED PHYSICS LETTERS 89, 031915-1 to 031915-3 (2006), ASTM D7709, ASTM F1249, ASTM398 and/or ASTME96, for their disclosure related to determining moisture permeability %, e.g., water vapor transfer rate (WVTR).

It can be desirable for a barrier element to have at least some transparency, such as at least 60% transparency, at least 70% transparency, at least 80% transparency, or at least 85% transparency. In some embodiments, the barrier element has a transparency of at least about 80%. See U.S. Pat. No. 8,169,136, for its disclosure related to determining total light transmission %.

In some embodiments, the barrier element layer containing the subject compound can comprise a polymer. In some embodiments, the barrier element can comprise a subject compound arranged in a layer. Some barrier elements can include a composite of a subject compound and a polymer material. For example, the subject compound can be disposed in the polymer material in such a manner as to create an exfoliated nanocomposite, an intercalated nanocomposite, or a phase-separated microcomposite. A phase-separated microcomposite phase can be achieved when, although mixed, the graphene exists as separate and distinct phases apart from the polymer. An intercalated nanocomposite can be achieved when the polymer compounds begin to intermingle amongst or between the graphene platelets but the graphene may not be distributed throughout the polymer. In an exfoliated nanocomposite phase, the individual graphene platelets can be distributed within or throughout the polymer. An exfoliated nanocomposite phase can be achieved by chemically exfoliating the graphene by a modified Hummer's method, a process well known to persons of ordinary skill in the art. In some embodiments, the majority of the graphene can be staggered to create an exfoliated nanocomposite as a dominant material phase. In some embodiments, the graphene material can be separated from adjacent graphene material within the polymer matrix by about 10 nm, about 50 nm, about 100 nm to about 500 nm or to about 1 micron.

In some embodiments, a subject compound can be in the form of sheets, planes, or flakes. In some embodiments, the graphene can have a surface area of between about 100-5000 m$^2$/gm, about 150-4000 m$^2$/gm, about 200-1000 m$^2$/gm, or about 400 m$^2$/gm-500 m$^2$/gm.

In some embodiments, more than about 90%, about 80%, about 70%, about 60% about 50%, about 40%, about 30%, about 20%, about 10% of the graphene material in the barrier element can be a subject compound. In other embodiments, the majority of the graphene material in the barrier element can be a subject compound. In still other embodiments, all of the graphene material in the barrier element can be a subject compound.

In some embodiments, the mass percentage of the subject compound relative to the total composition of the graphene containing layer can be between about 0.0001%-75% wt, about 0.001%-20% wt, or about 0.1%-1% wt.

In some embodiments, the polymer material can comprise crystalline polymer material and/or an amorphous polymer material. In some embodiments, the polymer crystals and chains that can be intercalated between the graphene sheets can provide separation of the sheets, and/or mechanical and chemical barriers to intruding fluid to substantially increasing the permeation distance resulting in increased gas barrier properties. In some embodiments, the polymer material can comprise a vinyl polymers, a biopolymer, or a combination thereof, with a possible exception of elastomeric, rubber and activated rubber. Examples of vinyl polymers may include polyvinyl butyral (PVB), polyvinyl alcohol (PVA), polyvinyl chloride (PVC), polyvinyl acetate (PVAc), polyacrylonitrile, ethylene vinyl alcohol (EVOH), and copolymers thereof; polyethyleneimine; poly(methyl methacrylate) (PMMA); vinyl chloride-acetate; and mixtures thereof. In some embodiments, the vinyl polymer can comprise PVA. In some embodiments, the biopolymers may include a collagen, hydrolyzed collagen or gelatin, acrylic gelatin, trisacryl gelatin, chitosan, and or proteins such as milk or whey proteins, or any combination thereof. Whey protein can be a mixture of about 65% beta-actoglobulin, about 25% alpha-lactalbumin, and/or about 8% serum albumin. In some embodiments, the gelatin can be either type A and type B gelatin or a mixture of both, where type A is derived from acid-cured tissue and type B is cured form lime-cured tissue. In some embodiments the biopolymer material can comprise gelatin, whey protein, chitosan, and/or mixtures thereof.

In some embodiments, the polymer material comprises an aqueous solution of about 2%-50% wt, about 2.5%-30% wt polymer, or about 5%-15% wt polymer.

In some embodiments, the barrier element can further comprise an acid, such as HCl, to catalyze a reaction between a group such as $CO_2H$ or OH and a group such as an amine.

In some embodiments, the barrier element can further comprise a dispersant. In some embodiments, the dispersant can be an ammonium salt, e.g., $NH_4Cl$; Flowlen; fish oil; long chain polymers; steric acid; oxidized Menhaden Fish Oil (MFO); dicarboxylic acids such as succinic acid, ethanedioic acid, propanedioic acid, pentanedioic acid, hexanedioic acid, heptanedioic acid, octanedioic acid, nonanedioic acid, decanedioic acid, o-phthalic acid, and p-phthalic acid; sorbitan monooleate; and mixtures thereof. Some embodiments preferably use oxidized MFO as a dispersant.

In some embodiments, the barrier element can further comprise at least a second organic binder, such as a vinyl polymer (e.g. polyvinyl butyral (PVB), polyvinyl alcohol (PVA), polyvinyl chloride (PVC), polyvinyl acetate (PVAc), polyacrylonitrile, mixtures thereof and copolymers thereof; polyethyleneimine; poly methyl methacrylate (PMMA); vinyl chloride-acetate; and mixtures thereof). In some embodiments, the organic binder can be PVB.

In some embodiments, the barrier element can further comprise a plasticizer. In some embodiments, the plasticizer can be a Type 1 Plasticizer—which can generally decrease the glass transition temperature ($T_g$) making it more flexible—phthalates (n-butyl, dibutyl, dioctyl, butyl benzyl, missed esters, and dimethyl); and/or a Type 2 Plasticizer—which can enable more flexibility, more deformable layers, and perhaps reduce the amount of voids resulting from lamination. Examples of Type 2 Plasticizers includes glycols (polyethylene; polyalkylene; polypropylene; triethylene; dipropylglycol benzoate).

Type 1 Plasticizers can include butyl benzyl phthalate, dicarboxylic/tricarboxylic ester-based plasticizers such as phthalate-based plasticizers such as bis(2-ethylhexyl) phthalate, diisononyl phthalate, bis(n-butyl)phthalate, butyl benzyl phthalate, diisodecyl phthalate, di-n-octyl phthalate, diisooctyl phthalate, diethyl phthalate, diisobutyl phthalate, di-n-hexyl phthalate and mixtures thereof; adipate-based plasticizers such as bis(2-ethylhexyl)adipate, dimethyl adipate, monomethyl adipate, dioctyl adipate and mixtures thereof; sebacate-based plasticizers such as dibutyl sebacate, and maleate.

Type 2 Plasticizers can include dibutyl maleate, diisobutyl maleate and mixtures thereof, polyalkylene glycols such as polyethylene glycol, polypropylene glycol and mixtures thereof. Other plasticizers which may be used include benzoates, epoxidized vegetable oils, sulfonamides such as N-ethyl toluene sulfonamide, N-(2-hydroxypropyl)benzene sulfonamide, N-(n-butyl)benzene sulfonamide, organophosphates such as tricresyl phosphate, tributyl phosphate, glycols/polyethers such as triethylene glycol dihexanoate, tetraethylene glycol diheptanoate and mixtures thereof; alkyl citrates such as triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, alkyl sulphonic acid phenyl ester and mixtures thereof.

A solvent can also be present in the barrier element. For example, the functionalized graphene material can be dispersed, dissolved and/or mixed with a solvent. Some solvents can be used in manufacture of material layers. In some embodiments, a solvent could include water; a lower alkanol such as ethanol, methanol, isopropyl alcohol; xylenes; cyclohexanone; acetone; toluene; methyl ethyl ketone; dimethylformamide; and/or mixtures thereof. Some embodiments can comprise xylene, ethanol and/or mixtures thereof. Other embodiments, the solvent can be dimethylformamide (DMF).

In some embodiments, the barrier element can be disposed between a substrate and a protective coating to create a barrier device. In some embodiments, the substrate and/or the protective coating can comprise a polymer. In some embodiments the polymer can comprise of vinyl polymers such as polyvinyl butyral (PVB), polyvinyl alcohol (PVA), polyvinyl chloride (PVC), polyvinyl acetate (PVAc), polyacrylonitrile, mixtures thereof and copolymers thereof; polyethyleneimine; poly methyl methacrylate (PMMA); vinyl chloride-acetate; and mixtures thereof.

A barrier element may be prepared by any suitable method, such as a method comprising dispersing the subject compound in one or more solvents and coating a substrate with the dispersion. The solvent used could include water or an aqueous mixture, an organic solvent such as dimethylformamide (DMF), or a solution comprising a polymer (used as a solvent or co-mixed with the subject compound in water, an aqueous solution, or an organic solvent). The dispersion of the subject compound in a solvent could be a solution, a suspension, or some other type of dispersion. In some embodiments, when a solution containing a subject compound is mixed with a solution containing a polymer, the mixing ratio can be between about 1:10, about 1:4, about 1:2, about 1:1, about 2:1, about 4:1, and about 10:1 parts graphene solution to polymer solution. Some embodiments preferably use a mixing ratio of about 1:1. In some embodiments, the graphene and polymer can be mixed such that the majority of the mixture comprises an exfoliated nanocomposite. One reason for using an exfoliated-nanocomposite phase is that in this phase the graphene platelets may be aligned such that permeability may be reduced in the finished film by elongating the possible molecular pathways through the film. In some embodiments, the graphene material can be suspended in an aqueous solution of between about 0.001% wt and about 0.08% wt. Some embodiments preferably use a graphene concentration of about 0.04% wt of the solution. In some embodiments the polymer can comprise a polymer in about a 5% to about 15% aqueous solution. Some embodiments use about a 10% aqueous solution.

In some embodiments, the method can comprise coating the substrate with the functionalized graphene material. In some embodiments, the method can comprise blade coating the dispersion on a substrate to create a thin film coated substrate, the thin film between about 0.05 µm to about 5 µm. The film can then be cast on a substrate to form a barrier element. In some embodiments, the casting can be done by co-extrusion, film deposition, blade coating or any other suitable method for deposition of a film on a substrate. In some embodiments, the mixture can be cast onto a substrate by blade coating (or tape casting) by using a doctor blade and dried to form a partial element. The thickness of the resulting cast tape can be adjusted by changing the gap between the doctor blade and the moving substrate. In some embodiments, the gap between the doctor blade and the moving substrate can be in the range of about 0.002 mm to about 1.0 mm or about 0.20 mm to about 0.50 mm. Meanwhile, the speed of the moving substrate can have a rate in the range of about 30 cm/min. to about 600 cm/min. By adjusting the moving substrate speed and the gap between the blade and moving substrate, the thickness of the resulting graphene polymer layer can be expected to be between about 0.05 µm and about 5 µm. In some embodiments, the thickness of the layer can be about 0.2 µm such that transparency can be maintained. The result is a barrier element.

Once a substrate is coated with a dispersion comprising the subject compound, the dispersion may be dried or allowed to dry. For example a substrate coated with a thin film of a dispersion comprising a subject compound could be dried for about 10 minutes to 1 hour at a temperature ranging from 20° C. to about 80° C. The drying can occur after deposition of the graphene layer on the substrate to remove the underlying solution from the graphene layer. In some embodiments, the drying temperature can be about room temperature, or 20° C., to about 120° C. In some embodiments the drying time can range from about 10 minutes to about 72 hours depending on the temperature. In some embodiments the drying time can range from about 10 minutes to about 1 hour depending at a temperature of about 20° C. to about 80° C. The purpose is to remove any solvent and precipitate the cast form. In some embodiments, drying is carried out at temperatures of about 60° C. for about 15 minutes.

In some embodiments, the method can comprise annealing the thin film coated substrate for about 10 hours to about 48 hours at a temperature ranging from about 40° C. to about 200° C. The dried barrier element can be isothermally crystallized, and/or annealed to enhance material properties. In some embodiments, annealing can be done from about 10 hours to about 80 hours at an annealing temperature of about 40° C. to about 200° C. In some embodiments, annealing can be done from about 10 hours to about 48 hours at an annealing temperature of about 40° C. to about 200° C. Some embodiments prefer that annealing can be accomplished at temperatures of about 100° C. for about 18 hours. Other embodiments prefer annealing done for 12 hours at 100° C.

After annealing, in some embodiments, the thin film coated substrate can be then optionally laminated with a protective coating layer to yield a barrier device. The construction can be in such a way that the graphene layer is sandwiched between the substrate and the protective layer. The method for adding layers can be by co-extrusion, film deposition, blade coating or any other suitable method. In some embodiments, additional layers may be added to enhance the properties of the barrier. In some embodiments, the protective layer is secured to the graphene with an adhesive layer to the barrier element to yield the barrier device. In other embodiments, the barrier element directly yields the barrier device.

Figure 2:
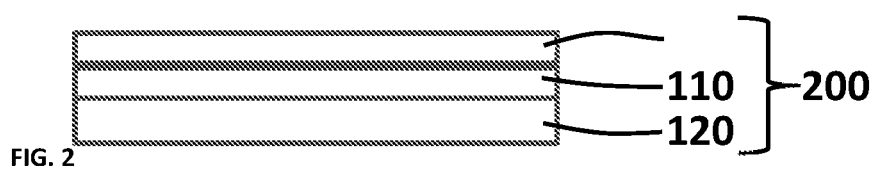
FIG. 2 is a schematic of an embodiment of a barrier device described herein.
Figure 3:
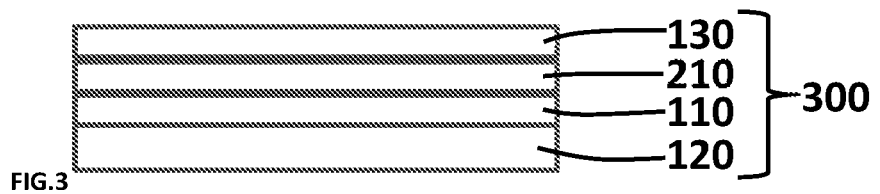
FIG. 3 is a schematic of an embodiment of a barrier device described herein.

In some embodiments, as seen in FIGS. 1, 2, and/or 3, barrier devices, 100, 200, and 200 comprise at least a substrate element, 120, and the aforementioned barrier element, 110. In some embodiments, a protective coating, 130, is provided on top of the barrier element. In some embodiments, additional layers are provided between the outer protective layer and the barrier element, such as an adhesive layer, 210. As a result of the layers, the barrier device can provide a transparent yet durable packaging system that is both gas and water resistant.

Figure 4:
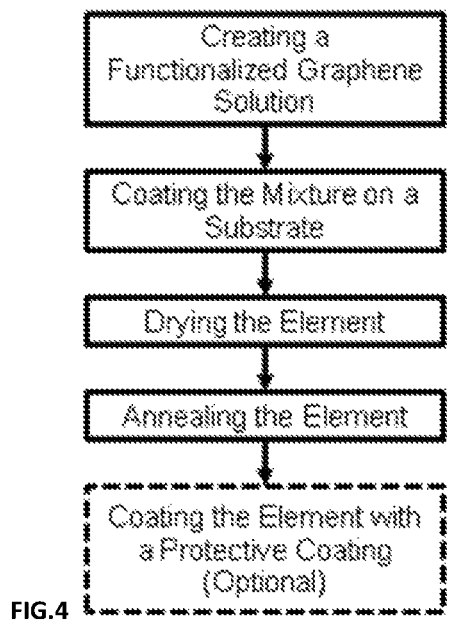
FIG. 4 is one possible embodiment for the process for making a nanocomposite barrier element and/or device.

As illustrated in FIG. 4, some methods for making a barrier element include: (a) creating a functionalized graphene solution and/or dispersion; (b) coating the functionalized solution and/or dispersion on a substrate; (c) drying the coated substrate; and (d) annealing the dried coated substrate.

First a solution of the functionalized graphene is obtained. The solution may include one or more solvents mixed in any number of ratios as described herein. Next, the mixture is coated onto a substrate. Coating may be achieved by blade coating, casting, spin coating, tape casting, etc. Next, the coated substrate is dried for a period of about 10 minutes to 72 hours and at a temperature of about 20° C. to about 120° C. The dried substrate is then annealed for about 10 hours to about 48 hours at a temperature ranging from about 40° C. to about 200° C. A protective coating may then be applied if desired.

Some embodiments include a method for making a transparent, barrier element comprising: (a) dispersing the subject compound in one or more solvents; (b) blade coating the dispersion on a substrate to create a thin film of between about 0.05 µm to about 5 µm; (c) drying the thin film coated substrate for about 10 minutes to 1 hour at a temperature ranging from 20° C. to about 80° C.; and (d) annealing the thin film coated substrate for about 10 hours to about 48 hours at a temperature ranging from about 40° C. to about 200° C. In some embodiments, the method further comprises laminating the thin film coated substrate with a protecting coating to yield a gas-barrier device.

The following embodiments are contemplated:

Embodiment 1. A graphene compound comprising an optionally functionalized graphene directly bonded to —NH—R—NHCOR' or —CO—NH—R—NHCOR';
wherein R is optionally substituted $C_{1-20}$ hydrocarbylene; and
R' is optionally substituted $C_{1-30}$ hydrocarbyl or $C_{3-30}$ heteroaryl.

Embodiment 2. The compound of embodiment 1, wherein the optionally functionalized graphene is a reduced graphene oxide.

Embodiment 3. The compound of embodiment 1, wherein the optionally functionalized graphene is a graphene oxide.

Embodiment 4. The compound of embodiment 1, 2, or 3, having a molar ratio of nitrogen to carbon that is about 0.001 to about 0.2.

Embodiment 5. The compound of embodiment 1, 2, or 3, having a molar ratio of nitrogen to carbon that is about 0.02 to about 0.1.

Embodiment 6. The compound of embodiment 1, 2, 3, 4, or 5, having molar ratio of oxygen to carbon that is about 0.01 to about 1.

Embodiment 7. The compound of embodiment 1, 2, 3, 4, or 5, having molar ratio of oxygen to carbon that is about 0.2 to about 0.8.

Embodiment 8. The compound of embodiment 1, 2, or 3, further represented by a formula $C_{100-200}H_{60-120}N_{1-10}O_{20-100}$.

Embodiment 9. The compound of embodiment 1, 2, 3, 4, 5, 6, 7, or 8, wherein R is $C_{1-12}$ alkylene.

Embodiment 10. The compound of embodiment 1, 2, 3, 4, 5, 6, 7, or 8, wherein R is $C_{6-10}$ alkylene.

Embodiment 11. The compound of embodiment 1, 2, 3, 4, 5, 6, 7, or 8, wherein R is —$(CH_2)_8$—.

Embodiment 12. The compound of embodiment 1, 2, 3, 4, 5, 6, 7, 8, 9, 10, or 11, wherein R' is $C_{1-4}$ alkyl.

Embodiment 13. The compound of embodiment 1, 2, 3, 4, 5, 6, 7, 8, 9, 10, or 11, wherein R' is —$CH_3$.

Embodiment 14. The compound of embodiment 1, 2, 3, 4, 5, 6, 7, 8, 12, or 13, wherein R is $C_{1-20}$ hydrocarbylene.

Embodiment 15. The compound of embodiment 1, 2, 3, 4, 5, 6, 7, 8, 9, 10, 11, or 14, wherein R' is $C_{1-20}$ hydrocarbylene.

Embodiment 16. The compound of embodiment 1, 2, 3, 4, 5, 6, 7, 8, 9, 10, 11, 12, 13, 14, or 15, wherein if the graphene is functionalized, any groups present on graphene are H, —OH, —O—, epoxy, =O, —CO$_2$H, COH, C$_{1-6}$—CO$_2$-alkyl (e.g. —CO$_2$CH$_3$, —CO$_2$C$_2$H$_5$, —CO$_2$C$_3$H$_7$, etc.), —O-alkyl (e.g. —O—CH$_3$, —O—C$_2$H$_5$, —O—C$_3$H$_7$, etc.), F, Cl, Br, CF$_3$, C$_{1-6}$ alkyl, CN, —NH—R—NH-COR', or —CO—NH—R—NHCOR'.

Embodiment 17. A barrier element comprising a compound of embodiment 1, 2, 3, 4, 5, 6, 7, 8, 9, 10, 11, 12, or 13, wherein the barrier element is transparent.

Embodiment 18. The barrier element of embodiment 14, wherein the barrier element has a gas permeability of less than 0.100 cc/m$^2$-day.

Embodiment 19. The barrier element of embodiment 14 or 15, wherein the element has a moisture permeability of less than 10.0 gm/m$^2$-day.

Embodiment 20. The barrier element of embodiment 14, 15, or 16, wherein the element has a transparency of at least about 80%.

Embodiment 21. The gas-barrier element of embodiment 14, 15, 16, or 17, wherein the element further comprises a protective coating.

Embodiment 22. A clear packaging comprising the compound or barrier element of embodiment 1, 2, 3, 4, 5, 6, 7, 8, 9, 10, 11, 12, 13, 14, 15, 16, 17, or 18.

Embodiment 23. A product wrapped in the clear packaging of embodiment 19.

EXAMPLE 1

N-(8-aminooctyl)acetamide (Intermediate Compound 1): A mixture of 9.3 g at 80 mmol n-butylacetate (Aldrich, St. Louis, Mo., USA), 11.4 g at 79 mmol 1,8-diaminooctane (Aldrich) with 4 mL de-ionized water was heated to reflux at 120° C. for 30 hrs. The resulted mixture was cooled down to room temperature and allowed to keep at room temperature for one day allowing the white crystalline solid to precipitate out. The resulting solid was washed with isopropanol (Aldrich) and filtered. The filtrate was collected and loaded on silica gel column, then purified by flash chromatography using eluents of ethylacetate (Aldrich) and isopropanol (Aldrich) in ratios of 7:3 to 3:7 to 0:1. The more polar desired fractions were collected and concentrated at below 30° C. After removal of solvents, white solid (IC-1) was obtained (5.8 g, in 40% yield). Confirmed by LCMS: calculated for C$_{10}$H$_{23}$N$_2$O (M+H): 187. Found: 187.

Barrier Compound-1 (BC-1): A solution of graphene oxide in water (100 ml of 0.4% wt) was added a solution of 500 mg IC-1 in 30 ml ethanol (Aldrich) while stirring. The resulting mixture was vigorously stirred for 24 hours, then purified by centrifuge and washing with deionized water three times followed by washing three times with methanol (Aldrich). The solid was collected by filtration and drying in a VWR 1400E vacuum oven (VWR International, Radnor, Pa.) at 60° C. for 48 hours to give 0.30 g of a black solid (BC-1). Elemental analysis: Calculated for [C$_{123}$H$_{82}$N$_4$O$_{70}$]$_n$: C, 54.00; H, 3.02; N, 2.05; O, 40.93. Found: C, 53.2; H, 3.1; N, 2.0; O, 41. 1H NMR (d7-DMF, d): 1.25. IR (KBr): 3450, 2980, 2920, 1640, 1470, 1238, 1100, 935, 895, 634.

EXAMPLE 2

Barrier Compound-2 (BC-2): To a solution of 100 ml of 0.4% wt. graphene oxide in water (Graphenea, Cambridge, Mass., USA) was added 500 mg of a solution of IC-1 in 25 ml methanol (Aldrich) while stirring. The resulting mixture was vigorous stirred at 50° C. for 24 hours. After cooled to room temperature, 1 mL of hydrazine monohydrate (Aldrich) was added and the mixture was stirred at room temperature for addition 24 hrs. The resulted suspension was centrifuged and washed with deionized water three times followed by washing with methanol (Aldrich) three times. The solid was collected by filtration and drying in VWR 1400E vacuum oven (VWR International, Radnor, Pa.) at 60° C. for 2 days to give 0.27 g of a black solid (BC-2). Elemental analysis: Calcd for [C$_{142}$H$_{102}$N$_8$O$_{35}$]$_n$: C, 68.76; H, 4.15; N, 4.52; O, 22.58. Found: C, 68.54; H, 4.02; N, 4.89; O, 22.55. IR (KBr): 3450, 2980, 2920, 1640, 1469, 1383, 1237, 1100, 962, 886, 632.

EXAMPLE 3

Creation of the Barrier Element Using BC-1

Barrier Element 1 (BE-1): Adding compound BC-1 and dispersing it in Dimethylformamide (DMF) (Alfa Aesar, Ward Hill, Mass., USA) to create a 0.04% wt. dispersion. Then, 10.0 g of the resulting aqueous dispersion was added to a mixture consisting of 10.0 g of 10% PVA aqueous solution (Aldrich), and 0.1 mL of 1N HCl aqueous solution (Aldrich). The resulting mixture was then stirred at room temperature for 16 hours.

Using the methods outlined above, the resulting compound was then tape cast onto a 125 µm thick poly(ethylene terephthalate) (PET) substrate (E Plastics, San Diego, Calif., USA) using a casting knife with a gap of 300 µm. Afterward, the substrate was put in a VMR 1400E oven (VWR International, Radnor, Pa.) at 60° C. for 15 minutes in order to remove any water and to precipitate the cast film, resulting in a film that was 0.2 µm thick. The resulting composite element was then annealed in an oven (VWR International, Radnor, Pa.) at 100° C. for 24 hours to yield Barrier Element-1 (BE-1).

COMPARATIVE EXAMPLE 1

Preparation of Barrier Element Using BC-1 without Thermal Treatment

In Comparative Example 1, Barrier Element CBE-3 was made in a similar manner as the element in Example 3, with the exception that after tape casting and drying the element was not further annealed. The result is that a barrier element was created, Comparative Barrier Element-3 (CBE-3).

EXAMPLE 4

Creation of Barrier Elements Using BC-2

In Example 4, Barrier Element 2 (BE-2) will be fabricated using the same methods outlined in Example 3 but compound BC-2 will be used instead of BC-1. The result is that a barrier element was created, Barrier Element-2 (BE-2).

COMPARATIVE EXAMPLE 2

Creation of Control Barrier Elements

To be able to isolate the impact of the barrier compounds, two additional comparative barrier elements were created which were comprised of the substrate and the PVA coating to serve as control elements. Comparative Barrier Element 1 (CBE-1) was a control element comprising a substrate of PET (E Plastics). In addition, Comparative Barrier Element 2 (CBE-2) was a control element that consisted of a substrate of PET (E Plastics) coated with a PVA tape using the methods outlined in Example 3 with the exception that a barrier compound was omitted from the mixture that was subsequently applied to the substrate to create a PVA tape.

EXAMPLE 5

Measurement of Barrier Elements

The barrier elements identified in Examples 1 through 4 and Comparative Examples 1 and 2 will each be examined to determine their optical characteristics as identified in their respective sections. The transparency of the barrier examples will be measured by adapting the methods taught in U.S. Pat. No. 8,169,136. The transparency of the barrier elements will be measured by high sensitivity multi channel photo detector (MCPD 7000, Otsuka Electronics Co., Ltd., Osaka, JP). First, a glass plate is irradiated with continuous spectrum light from a halogen lamp source (150 W, MC2563, Otsuka Electronics Co., Ltd.) to obtain reference transmission data. Next, each barrier element is to be placed on the reference glass and irradiated to determine transparency. The resulting transmission spectrum is then acquired by the photo detector (MCPD) for each sample. In this measurement, each barrier element on the glass plate will be coated with paraffin oil having the same refractive index as the glass plate. The transmittance at 800 nm wavelength of light will be used as a quantitative measure of transparency. The available/predicted results of the transparency measurements are presented in Table 1.

The barrier element's effectiveness in Examples 1 through 4 and Comparative Example 1 will also be measured by performing a Calcium-lifetime test which tests the water's permeability through the membrane. It is well known in the art that when pure Calcium metal, which is visible, is exposed to water it forms calcium hydroxide ($Ca(OH)_2$), a colorless crystal, and hydrogen gas.

To exploit this reaction to determine relative moisture permeability of the samples, pure calcium metal is heated to deposit on a class cover to form a 200 nm thick calcium film. The glass cover with calcium film is then encapsulated using a UV-curable epoxy resin (Epoxy Technology, Inc., Billerica, Mass., USA) with the pre-dried barrier elements in an inert atmosphere ($N_2$ gas, Airgas, San Marcos, Calif., USA). A control sample is also constructed by the same method using a barrier element but only constructed of glass. Then, the resulting samples will then be exposed to ambient conditions at 21° C. and 45% relative humidity to measure the calcium lifetime. The life time was determined when the Calcium, which was a dark metallic color, has mostly converted to calcium hydroxide, quantified when the sample becomes transparent. The available/predicted results of the calcium lifetime test are presented in Table 1.

TABLE 1

Transparency and Ca Lifetime for Various Examples.

| ID# | Description | Film Thickness [μm] | T % | Calcium Lifetime [hours] |
|---|---|---|---|---|
| CBE-1 | PET | 125 | 90.1 | 6 |
| CBE-2 | PVA/PET | 135 | 92.0 | 48 |
| CBE-3 | IC-1/PVA/PET (no thermal treatment) | 135.2 | 79.6 | 66 |
| BE-1 | IC-1/PVA/PET | 135.2 | 65.7 | 80 |
| BE-2 | IC-2/PVA/PET [1] | — | — | — |

Note [1]:
no measurements yet taken

EXAMPLE 6

Planned Measurements for $O_2$ and Water Vapor Testing

The Barrier Element samples will be tested for oxygen transmission rate (OTR) as described in ASTM D-3985, at a planned state of 23° C. and 0% relative humidity (RH) for a period of about 2 days using a MOCON Oxtran 2/21 oxygen permeability Instrument (Mocon, Minneapolis, Minn., USA).

In addition, the barrier element samples will be tested for water vapor transmission rate (WVTR) as described in ASTM F1249, at a planned state of 40° C. and 90% relative humidity (RH) for a period of about 2 days using a MOCON Permatran-W3/33 water vapor permeability instrument (Mocon).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A graphene compound comprising an optionally functionalized graphene, wherein the graphene is directly bonded to —NH—R—NHCOR' or —CO—NH—R—NH-COR';
   wherein R is optionally substituted $C_{1-20}$ hydrocarbylene;
   wherein R' is optionally substituted $C_{1-30}$ hydrocarbyl or $C_{3-30}$ heteroaryl; and
   wherein the graphene compound has a molar ratio of nitrogen to carbon that is about 0.001 to about 0.2.

2. The compound of claim 1, wherein the optionally functionalized graphene is a reduced graphene oxide.

3. The compound of claim 1, wherein the optionally functionalized graphene is a graphene oxide.

4. The compound of claim 1, wherein the molar ratio of nitrogen to carbon is about 0.02 to about 0.1.

5. A graphene compound comprising an optionally functionalized graphene, wherein the graphene is directly bonded to —NH—R—NHCOR' or —CO—NH—R—NH-COR';
   wherein R is optionallysubstituted $C_{1-20}$ hydrocarbylene;
   wherein R' is optionallysubstituted $C_{1-30}$ hydrocarbyl or $C_{3-30}$ heteroaryl; and
   wherein the graphene compound has a molar ratio of oxygen to carbon that is about 0.01 to about 1.

6. The compound of claim 5, wherein the molar ratio of oxygen to carbon is about 0.2 to about 0.8.

7. A graphene compound comprising an optionally functionalized graphene, wherein the graphene is directly bonded to —NH—R—NHCOR' or —CO—NH—R—NH-COR';
   wherein R is optionally substituted $C_{1-20}$ hydrocarbylene;
   wherein R' is optionally substituted $C_{1-30}$ hydrocarbyl or $C_{3-30}$ heteroaryl; and
   wherein the graphene compound is a compound of formula $C_{100-200}H^{60-120}N_{1-10}O_{20-100}$.

8. The compound of claim 1, wherein R is $C_{1-12}$ alkylene.

9. The compound of claim 1, wherein R is $C_{6-10}$ alkylene.

10. The compound of claim 1, wherein R is —$(CH_2)_8$—.

11. The compound of claim 1, wherein R' is $C_{1-4}$ alkyl.

12. The compound of claim 1, wherein R' is —$CH_3$.

13. A barrier element comprising a compound of claim 1, wherein the barrier element is transparent.

14. The barrier element of claim 13, wherein the barrier element has a gas permeability of less than 0.100 cc/m$^2$-day.

15. The barrier element of claim 13, wherein the element has a moisture permeability of less than 10.0 gm/m$^2$-day.

16. The barrier element of claim 13, wherein the element has a transparency of at least about 80%.

17. The compound of claim 4, wherein R' is —$CH_3$.

18. The compound of claim 6, wherein R' is —$CH_3$.

19. The compound of claim 7, wherein R' is —$CH_3$.

20. The compound of claim 8, wherein R' is —$CH_3$.

* * * * *